(12) United States Patent
Shenai-Khatkhate et al.

(10) Patent No.: US 7,547,631 B2
(45) Date of Patent: Jun. 16, 2009

(54) ORGANOMETALLIC COMPOUNDS

(75) Inventors: Deodatta Vinayak Shenai-Khatkhate, Danvers, MA (US); Qing Min Wang, North Andover, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 303 days.

(21) Appl. No.: 11/542,923

(22) Filed: Oct. 4, 2006

(65) Prior Publication Data

US 2008/0026577 A1    Jan. 31, 2008

Related U.S. Application Data

(60) Provisional application No. 60/834,479, filed on Jul. 31, 2006.

(51) Int. Cl.
*H01L 21/44* (2006.01)
*C23C 16/00* (2006.01)

(52) U.S. Cl. .................. 438/680; 106/1.25; 427/248.1; 438/681; 556/18; 556/20; 564/15

(58) Field of Classification Search .................. 556/18, 556/20; 438/680, 681; 427/248.1; 106/1.25; 564/15
See application file for complete search history.

(56) References Cited

U.S. PATENT DOCUMENTS

| | | | |
|---|---|---|---|
| 5,235,078 A | 8/1993 | Pohl et al. | |
| 5,502,128 A | 3/1996 | Flores et al. | |
| 5,707,913 A | 1/1998 | Schlund et al. | |
| 6,818,783 B2 | 11/2004 | Norman et al. | |
| 7,037,574 B2 | 5/2006 | Paranjpe et al. | |
| 2004/0033889 A1 | 2/2004 | Hessen et al. | |
| 2005/0042372 A1 | 2/2005 | Denk et al. | |
| 2005/0281952 A1 | 12/2005 | Xu et al. | |
| 2006/0035462 A1 | 2/2006 | Millward | |
| 2006/0046521 A1 | 3/2006 | Vaartstra et al. | |
| 2006/0110930 A1 | 5/2006 | Senzaki | |
| 2006/0141155 A1 | 6/2006 | Gordon et al. | |
| 2006/0148271 A1 | 7/2006 | Borovik et al. | |

FOREIGN PATENT DOCUMENTS

| | | |
|---|---|---|
| EP | 0 432 574 | 9/1996 |
| WO | WO 2004/000894 A1 | 12/2003 |
| WO | WO 2004/046417 A2 | 6/2004 |
| WO | 2006/012052 | 2/2006 |

OTHER PUBLICATIONS

Lim et al.; "Atomic Layer Deposition of Transition Metals"; Nature Materials, vol. 2, Nov. 2003, pp. 749-754.
Australian Search Report of corresponding Singapore Application No. 200705552-8; Mar. 1997.
Issleib et al., "Phospha-Amidine"; Journal of Organometallic Chemistry, vol. 160, 1978, pp. 47-57.
El-Ouatib et al., "Metallation reactions of diphosphiranes: new access to σ and π-diphosphaallyl complexes", Journal of Organometallic Chemistry, 453 (1993), pp. 77-84.
Appel et al., "Niederkoordinierte Phosphorverbindungen", Journal of Organometallic Chemistry, 319 (1987), pp. 345-350.
Lim et al., "Atomic Layer Deposition of Transition Metals"; Nature Materials, vol. 2(11), 2003, pp. 749-754.

*Primary Examiner*—Porfirio Nazario Gonzalez
(74) *Attorney, Agent, or Firm*—S. Matthew Cairns

(57) ABSTRACT

Organometallic compounds containing a phosphoamidinate ligand are provided. Such compounds are particularly suitable for use as vapor deposition precursors. Also provided are methods of depositing thin films, such as by ALD and CVD, using such compounds.

12 Claims, No Drawings

ORGANOMETALLIC COMPOUNDS

This application claims the benefit of U.S. Provisional Application Ser. No. 60/834,479, filed on Jul. 31, 2006.

The present invention relates generally to the field of organometallic compounds. In particular, the present invention relates to the field of organometallic compounds useful for chemical vapor deposition or atomic layer deposition of thin films.

In atomic layer deposition ("ALD") processes, conformal thin films are deposited by exposing a surface to alternating vapors of two or more chemical reactants. Vapor from a first precursor (or reactant) is brought to the surface onto which the desired thin film is to be deposited. Any unreacted vapor is then removed from the system under vacuum. Next, vapor from a second precursor is brought to the surface and allowed to react with the first precursor, with any excess second precursor vapor being removed. Each step in the ALD process typically deposits a monolayer of the desired film. This sequence of steps is repeated until the desired film thickness is obtained. In general, ALD processes are performed at fairly low temperatures, such as from 200 to 400° C. The exact temperature range will depend on the particular film to be deposited as well as on the particular precursors employed. ALD processes have been used to deposit pure metals as well as metal oxides, metal nitrides, metal carbide nitrides, and metal silicide nitrides.

ALD precursors must be sufficiently volatile to ensure a sufficient concentration of the precursor vapor in the reactor to deposit a monolayer on the substrate surface within a reasonable period of time. The precursors must also be sufficiently stable to be vaporized without premature decomposition and unwanted side reactions, but must also be sufficiently reactive to form the desired film on the substrate. With such a required balance of volatility and stability properties, there is an overall lack of suitable precursors.

Conventional precursors are homoleptic, i.e. they have a single ligand group. Homoleptic precursors offer uniform chemical characteristics, thus offering the inherent advantage of matching and harmonizing the functionality of ligand with the deposition process. However, the use of only a single ligand group offers less control over other paramount precursor characteristics, such as the shielding of metal center, that governs the surface reactions (e.g. chemisorption) and gas phase reaction (e.g. reaction with second complementary precursor), adjusting the volatility of precursor, and achieving required thermal stability for the precursor. For example, tetrakis(dialkylamino)hafnium is currently used as a chloride-free alternative to $HfCl_4$. However, this class of compound tends to produce premature decomposition of precursor either during the storage and/or before reaching the reactor. Substituting one or more of the dialkylamino groups with another organic group that imparts thermal stability has been tried but with little success, due to the inability to match the functionality of other group and achieve the desired stability. WO 2004/46417 (Gordon et al.) discloses certain amidinate compounds as suitable precursors for ALD. Such compounds may not provide the balance of volatility and thermal stability (or other properties) needed under certain ALD conditions. There remains a need for suitable and stable precursors that meet the deposition requirements and produce films that are essentially carbon-free.

The present invention provides an organometallic compound suitable for use as an ALD precursor having the formula $(R^1YCR^2PR^3)_n M^{+m} L^1_{(m-n)} L^2_p$, wherein $R^1$, $R^2$ and $R^3$ are independently chosen from H, $(C_1\text{-}C_6)$alkyl, $(C_2\text{-}C_6)$alkenyl, $(C_2\text{-}C_6)$alkynyl and aryl; Y=N or P; M=a metal; $L^1$=an anionic ligand; $L^2$=a neutral ligand; m=the valence of M; n=1-6; p=0-3; and wherein m≧n. Such compounds are suitable in a variety of vapor deposition methods, such as chemical vapor deposition ("CVD"), and are particularly suitable for ALD. Also provided is a composition including the above described compound and an organic solvent. Such a composition is particularly suitable for use in ALD and direct liquid injection processes.

Also provided by the present invention is a process of preparing phosphoamidine compounds including: reacting a nitrile compound with a primary phosphine in the presence of a metal trifluoromethanesulfonate catalyst. Optionally, a mixture of a primary phosphine and a primary amine may be used. The phosphoamidine compounds may be symmetrical or unsymmetrical.

The present invention further provides a method of depositing a film including the steps of: providing a substrate in a reactor; conveying the precursor compound described above in a gaseous form to the reactor; and depositing a film including the metal on the substrate. In another embodiment, the present invention provides a method of depositing a film including the steps of: providing a substrate in a reactor; conveying the first precursor compound described above in a gaseous form to the reactor; chemisorbing the first precursor compound on the surface of the substrate; removing any non-chemisorbed first precursor compound from the reactor; conveying a second precursor in a gaseous form to the reactor; reacting the first and second precursors to form a film on the substrate; and removing any unreacted second precursor.

As used throughout this specification, the following abbreviations shall have the following meanings, unless the context clearly indicates otherwise: ° C.=degrees centigrade; ppm=parts per million; ppb=parts per billion; RT=room temperature; M=molar; Me=methyl; Et=ethyl; i-Pr=iso-propyl; n-Bu=n-butyl; t-Bu=tert-butyl; c-Hx=cyclohexyl; Cp=cyclopentadienyl; COD=cyclooctadiene; CO=carbon monoxide; Bz=benzene; VTMS=vinyltrimethylsilane; THF=tetrahydrofuran; and PAMD=phosphamidinate.

"Halogen" refers to fluorine, chlorine, bromine and iodine and "halo" refers to fluoro, chloro, bromo and iodo. Likewise, "halogenated" refers to fluorinated, chlorinated, brominated and iodinated. "Alkyl" includes linear, branched and cyclic alkyl. Likewise, "alkenyl" and "alkynyl" include linear, branched and cyclic alkenyl and alkynyl, respectively. The articles "a" and "an" refer to the singular and the plural.

Unless otherwise noted, all amounts are percent by weight and all ratios are molar ratios. All numerical ranges are inclusive and combinable in any order except where it is clear that such numerical ranges are constrained to add up to 100%.

The organometallic compounds of the present invention, known generally as phosphoamidinates, have the general formula $(R^1YCR^2PR^3)_n M^{+m} L^1_{(m-n)} L^2_p$, wherein $R^1$, $R^2$ and $R^3$ are independently chosen from H, $(C_1\text{-}C_6)$alkyl, $(C_2\text{-}C_6)$alkenyl, $(C_2\text{-}C_6)$alkynyl and aryl; Y=N or P; M=a metal; $L^1$=an anionic ligand; $L^2$=a neutral ligand; m=the valence of M; n=1-6; p=0-3; and wherein m≧n. In one embodiment, each of $R^1$, $R^2$ and $R^3$ are independently chosen from methyl, ethyl, propyl, butyl, vinyl, allyl, butenyl, acetylenyl and propynyl. As used herein, "aryl" refers to an aromatic hydrocarbon radical, which optionally may have one or more of its hydrogens replaced with a substituent group such as, but not limited to, alkyl, alkenyl, alkoxy, and halo.

The subscript "n" represents the number of phosphoamidinate ligands in the present compounds. It will be appreciated by those skilled in the art that the phosphoamidinate ligand may be the only ligand in the present compounds.

A wide variety of metals may suitably be used to form the present phosphoamidinates. Typically, M is chosen from a Group 2 to Group 16 metal. As used herein, the term "metal" includes the metalloids boron, silicon, arsenic, selenium and tellurium but does not include carbon, nitrogen, phosphorus, oxygen and sulfur. In one embodiment, M=Be, Mg, Sr, Ba, Al, Ga, In, Si, Ge, Sb, Bi, Se, Te, Po, Cu, Zn, Sc, Y, La, a lanthanide metal, Ti, Zr, Hf, Nb, W, Mn, Co, Ni, Ru, Rh, Pd, Ir or Pt. In another embodiment, M=Al, Ga, In, Ge, La, a lanthanide metal, Ti, Zr, Hf, Nb, W, Mn, Co, Ni, Ru, Rh, Pd, Ir or Pt.

A wide variety of anionic ligands ($L^1$) may be used in the present invention. Such ligands bear a negative charge. Possible ligands include, without limitation, Ligands (reactive towards surface and in gas phase): hydride, halide, azide, alkyls, alkenyl, alkynyl, carbonyl, amido, alkylamino, dialkylamino, dialkylaminoalkyl, imino, hydrazido, phosphido, nitrosyl, nitryl, nitrite, nitrate, nitrile, alkoxy, dialkylaminoalkoxy, alkoxyalkyldialkylamino, siloxy, diketonates, ketoiminates, cyclopentadienyls, silyls, pyrazolates, guanidinates, phosphoguanidinates and amidinates. Any of such ligands may be optionally substituted such as by replacing one or more hydrogens with another substituent group such as halo, amino, disilylamino and silyl. Exemplary anionic ligands include, but are not limited to: ($C_1$-$C_{10}$)alkyl such as methyl, ethyl, propyl, butyl, pentyl, hexyl, cyclopropyl, cyclopentyl and cyclohexyl; ($C_2$-$C_{10}$)alkenyl such as ethenyl, allyl, and butenyl; ($C_2$-$C_{10}$)alkynyl such as acetylenyl and propynyl; ($C_1$-$C_{10}$)alkoxy such as methoxy, ethoxy, propoxy, and butoxy; ($C_1$-$C_{10}$)alkylamino such as methylamino, ethylamino and propylamino; di($C_1$-$C_{10}$)alkylamino such as dimethylamino, diethylamino, ehtylmethylamino and dipropylamino; cyclopentadienyls such as cyclopentadienyl, methylcyclopentadienyl and pentamethylcyclopentadienyl; di($C_1$-$C_{10}$)alkylamino($C_1$-$C_{10}$)alkoxy such as dimethylaminoethoxy, diethylaminoethoxy, dimethylaminopropoxy, ethylmethylaminopropoxy and diethylaminopropoxy; silyls such as ($C_1$-$C_{10}$)alkylsilyls and ($C_1$-$C_{10}$)alkylaminosilyls; and alkyl amidinates such as N,N'-dimethyl-methylamidinato, N,N'diethyl-methylamidinato, N,N'-diethyl-ethylamidinato, N,N'-di-iso-propyl-methylamidinato, N,N'-di-iso-propyl-iso-propylamidinato, and N,N'-dimethyl-phenylamidinato. When 2 or more anionic ligands are present, such ligands may be the same or different.

Neutral ligands ($L^2$) are optional in the present compounds. Such neutral ligands do not bear an overall charge and may function as stabilizers. Neutral ligands include, without limitation, CO, NO, alkenes, dienes, trienes, alkynes, and aromatic compounds. Exemplary neutral ligands include, but are not limited to: ($C_2$-$C_{10}$)alkenes such as ethene, propene, 1-butene, 2-butene, 1-pentene, 2-pentene, 1-hexene, 2-hexene, norbornene, vinylamine, allylamine, vinyltri($C_1$-$C_6$)alkylsilane, divinyldi($C_1$-$C_6$)alkylsilane, vinyltri($C_1$-$C_6$)alkoxysilane and divinyldi($C_1$-$C_6$)alkoxysilane; ($C_4$-$C_{12}$) dienes such as butadiene, cyclopentadiene, isoprene, hexadiene, octadiene, cyclooctadiene, norbornadiene and α-terpinene; ($C_6$-$C_{16}$)trienes; ($C_2$-$C_{10}$)alkynes such as acetylene and propyne; and aromatic compounds such as benzene, o-xylene, m-xylene, p-xylene, toluene, o-cymene, m-cymene, p-cymene, pyridine, furan and thiophene. The number of neutral ligands depends upon the particular metal chosen for M. When 2 or more neutral ligands are present, such ligands may be the same or different.

The present phosphoamidinates may be prepared by a variety of methods known in the art. For example, the general procedure disclosed in U.S. Patent Application No. 2004/0033889 (Hessen et al.) for the manufacture of certain yttrium arylphosoamidinates may be employed to prepare the present non-aryl phosphoamidinates. The term "non-aryl phosphoamidinates" refers to a phosphoamidinate compound that does not have any aryl substitution on the phosphoamidinate ligand. Alternatively, the general procedures disclosed in U.S. Pat. No. 5,502,128 (Rausch et al.) and International Patent Application WO 2004/46417 for the manufacture of certain amidinates may be easily modified by those skilled in the art to prepare the present phosphoamidinates. In one embodiment, the present compounds may be prepared by reacting a phosphoamidinate lithium salt with a metal halide in a suitable solvent such as hexane. Such reaction may be performed over a range of temperatures, with room temperature being suitable for certain reactions. In an alternate synthesis of the present compounds, an alkyl lithium may be first reacted with a metal halide in a suitable solvent, such as THF, and at a suitable temperature, such as room temperature, followed by reaction with a phosphoamidine in a suitable solvent, typically the same solvent as used for the first reaction.

Alternatively, phosphoamidines may be prepared by reacting a suitable nitrile compound with a primary phosphine in the presence of a metal trifluoromethanesulfonate catalyst. Exemplary nitrile compounds are those having the formula $R^2$—C≡N or $R^2$NH—C≡N. Exemplary primary phosphines have the formula $R^3PH_2$. Optionally, a mixture of a primary phosphine and a primary amine is used. Exemplary primary amines have the formula $R^1NH_2$. Each of $R^1$, $R^2$ and $R^3$ is independently chosen from H, ($C_1$-$C_6$)alkyl, ($C_2$-$C_6$)alkenyl, ($C_2$-$C_6$)alkynyl and aryl. Suitable metal trifluoromethanesulfonate catalysts have the formula $M(CF_3SO_3)_3$, where M is a metal, such as lanthanum or any metal in the lanthanide group. Such phosphoamidines can be symmetrical or unsymmetrical. The above process can be a one-pot or step-wise co-condensation. The phosphoamidine compounds prepared by the above reaction typically has the formula $H(R^1YCR^2PR^3)$, wherein $R^1$, $R^2$ and $R^3$ are independently chosen from H, ($C_1$-$C_6$)alkyl, ($C_2$-$C_6$)alkenyl, ($C_2$-$C_6$)alkynyl and aryl; Y=N or P. The above reaction utilizing a nitrile of formula $R^2$—C≡N is summarized in the following reaction sequence, where Y=N or P; $R^1$ may be the same as or different from $R^3$.

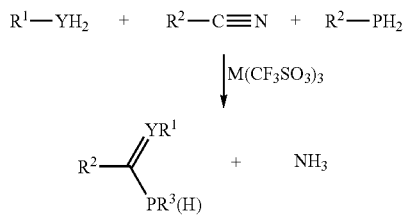

The above reaction utilizing a nitrile of formula $R^2$—NH—C≡N is summarized in the following reaction sequence, where Y=N or P; $R^1$ may be the same as or different from $R^3$.

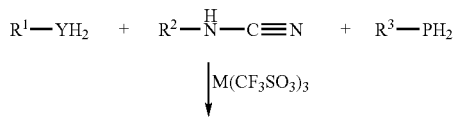

-continued

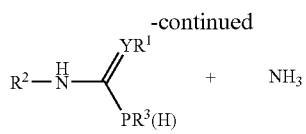
+ NH$_3$

Exemplary primary phosphines include, without limitation, methylphosphine, ethylphosphine, iso-propylphosphine, iso-butylphosphine, tert-butylphosphine and phenylphosphine. Primary phosphines are generally commercially available, such as from Aldrich Chemical Company (Milwaukee, Wis.) or may be prepared by a variety of methods known in the literature, such as by using Grignard reagents as disclosed in U.S. Pat. No. 6,939,983 (Shenai-Khatkhate et al.) or based on organolithium and/or organoaluminum reactions as disclosed in U.S. Pat. No. 6,956,127 (Shenai-Khatkhate et al.). Exemplary primary amines include, but are not limited to, methylamine, ethylamine, n-propylamine, iso-propylamine, and tert-butylamine. Such primary amines are generally commercially available, such as from Aldrich Chemical Company The phosphoamidine compounds may be prepared by combining the suitable nitrile compound, primary phosphine, metal trifluoromethanesulfonate catalyst and optional primary amine in any order. Optionally, an organic solvent may be used. The reaction may be performed at a variety of temperatures, such as at reflux. Typically, the reaction is complete within several hours.

In an alternative synthesis route for phosphoguanidine, a primary phosphine and carbodiimide are reacted in the presence of a metal trifluoromethanesulfonate catalyst. Any of the above described metal trifluoromethanesulfonate catalyst may be used. The reaction conditions are similar to those described above for the phosphoamidine compounds. The preparation of phosphoguanidine compounds is illustrated below, where $R^1$, $R^2$ and $R^3$ have the meaning ascribed above.

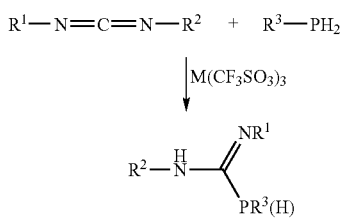

The present metal phosphoamidinate organometallic compounds can be prepared by the metathesis reaction of metal salts (generally halides) with alkali metal phosphoamidinates. Alkali metal phosphoamidinates may be prepared by reacting a phosphoamidine compound with either an alkyl alkali metal reagent (such as n-butyl lithium, methyl lithium and tertiary butyl lithium), an alkali metal hydride (such as sodium hydride and potassium hydride) or an alkali metal amide (such as sodium amide). Alternatively, metal phosphoamidinates can be prepared by the exchange reaction between metal dialkylamides and free phosphoamidine in the presence of an organic solvent. The above reactions are generally carried out under inert atmosphere, such as under nitrogen, argon or a mixture thereof. Typically, the organic solvents used in such reactions are substantially free of metallic and oxygenated impurities.

The present organometallic compounds are particularly suitable for use as precursors for the vapor phase deposition of thin films. Such compounds may be used in a variety of CVD processes as well as in a variety of ALD processes. In one embodiment, 2 or more of such organometallic compounds may be used in a CVD or ALD process. When 2 or more organometallic compounds are used, such compounds may contain the same metal but having different ligands, or may contain different metals. In another embodiment, one or more of the present organometallic compounds may be used with one or more other precursor compounds.

Bubblers (also known as cylinders) are the typical delivery devices used to provide the present organometallic compounds in the vapor phase to a deposition reactor. Such bubblers typically contain a fill port, a gas inlet port and an outlet port which is connected to a deposition chamber. A carrier gas typically enters the bubbler through the gas inlet port and entrains or picks up precursor vapor. The entrained or carried vapor then exits the bubbler through the outlet port and is conveyed to the deposition chamber. A variety of carrier gases may be used, such as hydrogen, helium, nitrogen, argon and mixtures thereof.

A wide variety of bubblers may be used, depending upon the particular deposition apparatus used. When the precursor compound is a solid, the bubblers disclosed in U.S. Pat. No. 6,444,038 (Rangarajan et al.) and U.S. Pat. No. 6,607,785 (Timmons et al.), as well as other designs, may be used. For liquid precursor compounds, the bubblers disclosed in U.S. Pat. No. 4,506,815 (Melas et al) and U.S. Pat. No. 5,755,885 (Mikoshiba et al) may be used, as well as other liquid precursor bubblers. The source compound is maintained in the bubbler as a liquid or solid. Solid source compounds are typically vaporized or sublimed prior to transportation to the deposition chamber. Bubbler for use with ALD processes may have pneumatic valves at the inlet and outlet ports to facility opening and closing as required to provide the necessary vapor pulses.

In conventional CVD processes, a bubbler for supplying a liquid precursor, as well as certain bubblers for supplying solid precursors, will contain a dip tube which is connected to the gas inlet port. In general, the carrier gas is introduced below the surface of the organometallic compound, also called a precursor or source compound, and travels upward through the source compound to the headspace above it, entraining or carrying vapor of the source compound in the carrier gas.

Precursors used in ALD processes are often liquids, low melting solids, or solids formulated in a solvent. To handle these types of precursors, bubblers used in ALD processes may contain a dip tube connected to the outlet port. Gas enters these bubblers through the inlet, pressurizes the bubbler and forces the precursor up the dip tube and out of the bubbler.

The present invention provides a delivery device including the organometallic compound described above. In one embodiment, the delivery device includes a vessel having an elongated cylindrical shaped portion having an inner surface having a cross-section, a top closure portion and a bottom closure portion, the top closure portion having an inlet opening for the introduction of a carrier gas and an outlet opening, the elongated cylindrical shaped portion having a chamber containing the organometallic compound described above.

In an embodiment, the present invention provides a device for feeding a fluid stream saturated with an organometallic compound of the formula $(R^1YCR^2PR^3)_n M^{+m} L^1_{(m-n)} L^2_p$, wherein $R^1$, $R^2$ and $R^3$ are independently chosen from H, $(C_1-C_6)$alkyl, $(C_2-C_6)$alkenyl, $(C_2-C_6)$alkynyl and aryl; Y=N or P; M=a metal; $L^1$=an anionic ligand; $L^2$=a neutral ligand; m=the valence of M; n=1-6; p=0-3; and wherein m≧n to a chemical vapor deposition system including a vessel having an elongated cylindrical shaped portion having an inner surface having a cross-section, a top closure portion and a bottom closure portion, the top closure portion having an inlet opening for the introduction of a carrier gas and an outlet opening, the elongated cylindrical shaped portion having a chamber containing the organometallic compound; the inlet opening being in fluid communication with the chamber and the chamber being in fluid communication with the outlet opening. In a still further embodiment, the present invention provides an apparatus for chemical vapor deposition of metal films including one or more devices for feeding a fluid stream saturated with the organometallic compound described above.

The deposition chamber is typically a heated vessel within which is disposed at least one, and possibly many, substrates. The deposition chamber has an outlet, which is typically connected to a vacuum pump in order to draw by-products out of the chamber and to provide a reduced pressure where that is appropriate. Metalorganic CVD ("MOCVD") can be conducted at atmospheric or reduced pressure. The deposition chamber is maintained at a temperature sufficiently high to induce decomposition of the source compound. The typical deposition chamber temperature is from 200° to 1200° C., more typically from 200° to 600° C., the exact temperature selected being optimized to provide efficient deposition. Optionally, the temperature in the deposition chamber as a whole can be reduced if the substrate is maintained at an elevated temperature, or if other energy such as plasma is generated by a radio frequency source.

Suitable substrates for deposition, in the case of electronic device manufacture, may be silicon, silicon germanium, silicon carbide, gallium nitride, gallium arsenide, indium phosphide, and the like. Such substrates are particularly useful in the manufacture of integrated circuits.

Deposition is continued for as long as desired to produce a film having the desired properties. Typically, the film thickness will be from several hundred to several thousand angstroms or more when deposition is stopped.

Thus, the present invention provides a method for depositing a metal film including the steps of: a) providing a substrate in a vapor deposition reactor; b) conveying as a precursor the organometallic compound described above is a gaseous form to the reactor; and c) depositing a film including the metal on the substrate. In a typical CVD process, the above described method further includes the step of decomposing the precursor in the reactor.

Thin metal-containing films are produced by ALD with almost perfect stoichiometry by alternately subjecting the substrate, one at a time, to the vapor of precursor compounds of each of the elements of which the film is formed. In ALD processes, a substrate is subjected to the vapor of a first precursor which can react with the surface of the substrate at a temperature sufficiently high for such reaction to occur whereby a single atomic layer of the first precursor (or metal contained therein) is formed on the surface of the substrate, and subjecting the thus formed surface with the first precursor atomic layer thereon to the vapor of a second precursor which reacts with the first precursor at a temperature sufficiently high for such reaction to occur whereby a single atomic layer of the desired metal film is formed on the surface of the substrate. This procedure can be continued by alternately using the first and second precursors until the film that is formed reaches a desire to thickness. The temperatures used in such ALD processes are typically lower than those employed in MOCVD process and may be in the range of 200 to 400° C., although other suitable temperatures may be employed depending-upon the precursors chosen, the film to be deposited, and on other criteria known to those skilled in the art.

An ALD apparatus typically includes a vacuum chamber means to provide an evacuated atmosphere, a pair of means situated in the vacuum chamber means, the pair of means including a support means for supporting at least one substrate and a source means for forming sources for as least two vapors of two different precursors, respectively, and operating means operatively connected with one of the pair of means for operating the one means with respect to the other of the pair of means for providing on the substrate first a single atomic layer of one of the precursors and then a single atomic layer of the other precursor. See, e.g., U.S. Pat. No. 4,058,430 (Suntola) for a description of an ALD apparatus.

In a further embodiment, the present invention provides a method of depositing a film including the steps of: providing a substrate in a vapor deposition reactor; conveying as a first precursor the organometallic compound described above in a gaseous form to the reactor; chemisorbing the first precursor compound on the surface of the substrate; removing any non-chemisorbed first precursor compound from the reactor; conveying a second precursor in a gaseous form to the reactor; reacting the first and second precursors to form a film on the substrate; and removing any unreacted second precursor. The alternating steps of conveying the first and second precursors and step of reacting the first and second precursors being repeated until a film of the desired thickness is obtained. The step of removing a precursor from the reactor may include one or more of evacuating the reactor under vacuum and purging the reactor using a non-reactant gas and/or solvent vapor. The second precursor may be any suitable precursor that reacts with the first precursor to form the desired film. Such second precursors may optionally contain another metal. Exemplary second precursors include, but are not limited to, oxygen, ozone, water, peroxide, alcohols, nitrous oxide and ammonia.

When the present organometallic compounds are to be used in ALD processes or in direct liquid injection processes, they may be combined with an organic solvent. Any organic solvent which is suitably inert to the organometallic compound can be used. Exemplary organic solvents include, without limitation, aliphatic hydrocarbons, aromatic hydrocarbons, linear alkyl benzenes, halogenated hydrocarbons, silyated hydrocarbons, alcohols, ethers, glymes, glycols, aldehydes, ketones, carboxylic acids, sulphonic acids, phenols, esters, amines, alkylnitrile, thioethers, thioamines, cyanates, isocyanates, thiocyanates, silicone oils, nitroalkyl, alkylnitrate, and mixtures thereof. Suitable solvents include tetrahydrofuran, diglyme, n-butyl acetate, octane, 2-methoxyethyl acetate, ethyl lactate, 1,4-dioxane, vinyltrimethylsilane, pyridine, mesitylene, toluene, and xylene. Mixtures of organic solvents may be used. When used in direct liquid injection processes, the concentration of the organometallic compound is typically in the range of 0.05 to 0.25 M, and more typically 0.05 to 0.15M. The organometallic compound/organic solvent compositions may be in the form of solutions, slurries or dispersions.

Compositions including the present organometallic compound and an organic solvent are suitable for use in vapor deposition processes employing direct liquid injection. Suitable direct liquid injection processes are those described in U.S. patent application No. 2006/0110930 (Senzaki).

Further provided by the present invention is a method for manufacturing an electronic device including the step of depositing a metal-containing film using any one of the above described methods.

The present invention provides an enabling solution to the use of heteroleptic precursors for vapor deposition, particularly ALD, which have a suitable balance of functionality, desired thermal stability, appropriate metal center shielding and well governed surface as well as gas phase reactions, by use of phosphoamidinate ligands.

The following examples are expected to illustrate various aspects of the present invention.

EXAMPLE 1

Di-iso-propyl phosphoamidine is expected to be synthesized as follows.

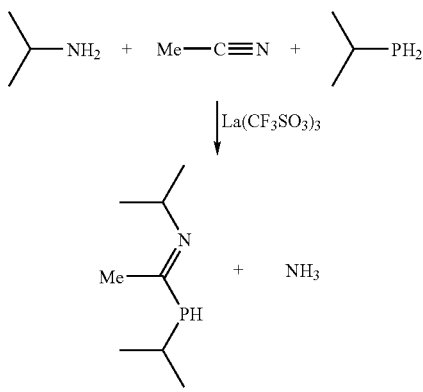

A solution of equimolar mixture of iso-propyl amine, iso-propyl phosphine, and acetonitrile is mixed with lanthanum triflate (1 to 2%) in a pressure vessel at atmospheric pressure and under inert atmosphere. An excess of acetonitrile (10 to 25%) is used as solvent and is expected to aid in homogenizing the reaction mass. The pressure vessel is then heated to 50 to 60° C. in an isothermal chamber or oven for 5 to 6 hours with constant stirring of the reaction mass. Alternatively, this reaction may be carried out at atmospheric pressures and under reflux conditions. The ammonia released during the reaction is scrubbed using commercial scrubbers (destructive removal efficiency >99%) before venting to atmosphere. Excess solvent and by-products are expected to be removed by vacuum distillation. The resulting expected di-iso-propylphosphoamidine is then distilled under vacuum. The product is expected to be obtained in high yields (>75%), and free of organic and metallic impurities as detected by FT-NMR and ICP-MS.

EXAMPLE 2

(Di-iso-propyl phosphoamidinato)lithium is expected to be synthesized as follows.

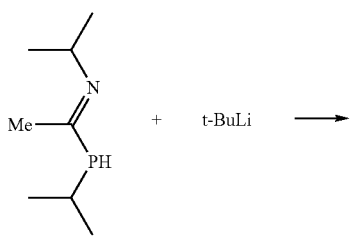

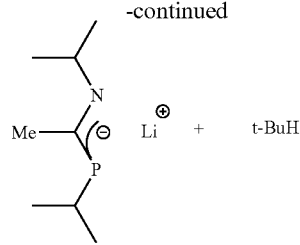

The lithium salt of di-iso-propyl phosphoamidine is prepared by reacting at −78° C. a hexane solution of n-butyl-lithium (2.3 M in hexane) with an equimolar quantity of di-iso-propyl phosphoamidine dissolved in ethereal solvent. The addition is carried out in a dropwise manner and with efficient stirring. After completing the addition, the reaction mixture is allowed to attain room temperature. The solvents and unreacted reagents are expected to be removed using vacuum stripping. The product is then dissolved in butyldiglyme ("BDG") to obtain a solution of di-iso-propyl phosphoamidinato lithium (25 to 50%).

EXAMPLE 3

(Di-iso-butyl phosphoamidinato)lithium is expected to be synthesized using the procedures of Examples 1 and 2, and employing iso-butyl amine and iso-butyl phosphine.

EXAMPLE 4

Unsymmetrical mono(N-iso-propyl-P-t-butyl phosphoamidinato)lithium is expected to be synthesized using the procedures of Examples 1 and 2, and employing iso-propyl amine and tertiary-butyl phosphine.

EXAMPLE 5

Unsymmetrical mono(N-tert-butyl-P-iso-butyl phosphoamidinato)sodium is expected to be synthesized using the procedures of Examples 1 and 2, and employing tert-butyl amine and iso-butyl phosphine, and employing sodium amide in butyl diglyme instead of n-butyl lithium in hexane.

EXAMPLE 6

Tetrakis(di-iso-propyl phosphoamidinato)hafnium, Hf(iPr-PAMD)$_4$, is expected to be synthesized by reacting the tetrakis(ethylmethylamino)hafnium with 4.4 molar excess of di-iso-propyl phosphoamidinate (obtained from Example 1) in toluene at elevated temperature (not exceeding 100° C.) for 6 hours. After complete reaction, the reaction mass is allowed to cool to room temperature. Upon further cooling to 0° C. and below, the target product tetrakis(di-iso-propyl phosphoamidinato)hafnium is expected to be obtained in high yields.

EXAMPLE 7

Tris(di-iso-propyl phosphoamidinato)aluminum, Al(iPr-PAMD)$_3$, is expected to be synthesized by reacting the tris(ethylmethylamino)aluminum with 3.3 molar excess of di-iso-propyl phosphoamidinate (obtained from Example 1) in toluene at elevated temperature (not exceeding 80° C.) for 5 hours. After complete reaction, the reaction mass is allowed to cool to room temperature. Upon further cooling to 0° C.

and below, the target product tris (di-iso-propyl phosphoamidinato)aluminum is expected to be obtained in high yields.

EXAMPLE 8

Tetrakis(di-iso-butyl phosphoamidinato)germaniuum, Ge(iBu-PAMD)$_4$, is expected to be synthesized by reacting the germanium tetrachloride with 4.5 molar excess of lithium salt of di-iso-butyl phosphoamidine (obtained from Example 3) in BDG at elevated temperature (not exceeding 100° C.) for 5 hours. After complete reaction, the reaction mass is allowed to cool to room temperature. Upon further cooling the solution to 0° C., the target product tetraks(di-iso-butyl phosphoamidinato)germanium is expected to be obtained in high yields.

EXAMPLE 9

Unsymmetrical tris(N-iso-propyl-P-t-butyl phosphoamidinato)antimony is expected to be synthesized by reacting the mono(N-iso-propyl-P-t-butyl phosphoamidinato)lithium (obtained from Example 4) with antimony trichloride (3.3:1 molar ratio) in n-butyl ether at elevated temperature (not exceeding 80° C.) for 8 hours. After complete reaction, the reaction mass is allowed to cool to room temperature. Upon further cooling the solution to 0° C., the target product unsymmetrical tris(N-iso-propyl-P-t-butyl phosphoamidinato)antimony is expected to be obtained in high yields.

EXAMPLE 10

Unsymmetrical bis(N-tert-butyl-P-iso-butyl phosphoamidinato)tetrakis (ethylmethylamido)tungsten is expected to be synthesized by reacting the mono (N-tert-butyl-P-iso-butyl phosphoamidinato)sodium (obtained from Example 5) and lithium ethylmethylamide with tungsten hexaachloride (2:4:1 molar ratio) in BDG at elevated temperature (not exceeding 100° C.) for 6 hours. After complete reaction, the reaction mass is allowed to cool to room temperature. Upon further cooling the solution to 0° C., the target product unsymmetrical (N-tert-butyl-P-iso-butyl phosphoamidinato) tetrakis(ethylmethylamido)tungsten is expected to be obtained in high yields.

EXAMPLE 11

Tetrakis(di-ethyl phosphoamidinato)tellurium, Te(Et-PAMD)$_4$, is expected to be synthesized by reacting the tetrakis(ethylmethylamino)tellurium with 4.4 molar excess of diethyl phosphoamidine (following the procedures of Example 1) in toluene at elevated temperature (not exceeding 100° C.) for 6 hours. After complete reaction, the reaction mass is allowed to cool to room temperature. Upon further cooling to 0° C. and below, the target product tetrakis(diethyl phosphoamidinato)tellurium is expected to be obtained in high yields. The product may contain bis(diethylphosphoamidinato)tellurium as a secondary product.

EXAMPLE 12

Bis(isopropylphosphoamidinato)ruthenocene, [MeCP(i-Pr)N(i-Pr)]$_2$Ru(Cp), is expected to be synthesized as follows:

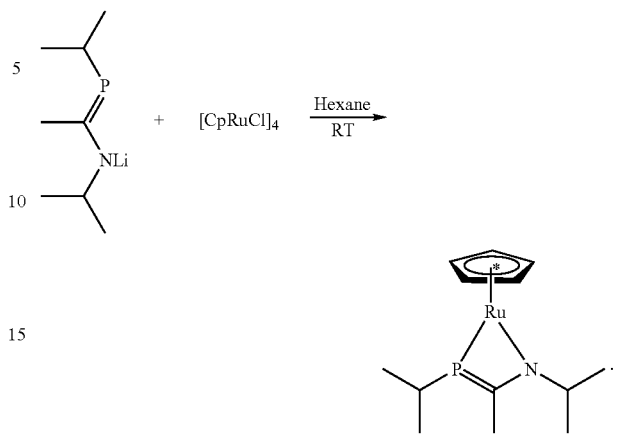

The lithium salt of isopropylphosphoamidinate is reacted with cyclopentadienyl ruthenium chloride tetramer in hexane at room temperature (approximately 25° C.), employing slight molar excess (1-2%) than required by stoichiometry. The reaction is carried out under an inert atmosphere of nitrogen, in a 3-neck round bottom flask equipped with magnetic or mechanical stirring and effective heating/cooling system to control the rate of reaction. The reagents are added in continuous and dropwise manner, and are allowed to mix slowly to control the exothermicity of the reaction. The reaction mass is maintained below 60-80° C. After completing the addition, the reaction mixture is stirred for 1 hour at room temperature. The reaction mass is heated to obtain a gentle reflux to ensure complete reaction. The crude product is then expected to separate from the reaction mass upon cooling, and is then to be purified using standard distillation and/or recrystallization techniques. The target product bis(isopropylphosphoamidinato) ruthenocene is expected to be obtained in high yield and is expected to be substantially free of organic solvents (<0.5 ppm) as determined by FT-NMR and also substantially free of metallic impurities (<10 ppb) as determined by ICPMS/ICP-OES.

EXAMPLE 13

Trimethylsilylmethyl-bis(isopropylphosphoamidinato) lanthanum, [MeCP(i-Pr)N(i-Pr)]$_2$La(CH$_2$SiMe$_3$), is expected to be synthesized as follows:

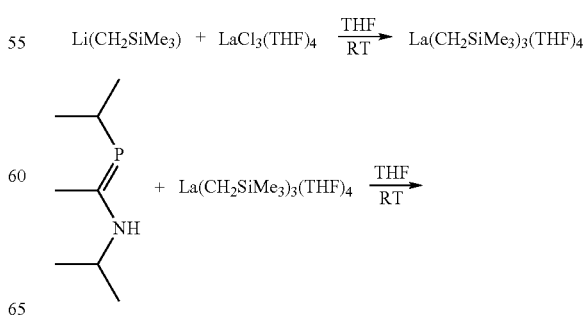

-continued

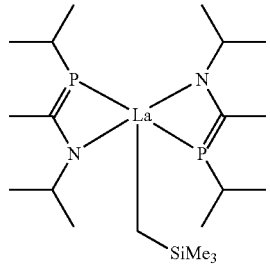

The lithium salt (trimethylsilylmethyl lithium) is reacted with the THF adduct of lanthanum trichloride in THF at room temperature (approximately 25° C). The intermediate product is then reacted with free isopropyl phosphoamidine in THF to obtain the target product trimethylsilylmethyl-bis (isopropylphosphoamidinato)lanthanum. The reaction is expected to be a batch operation, and a one-pot-synthesis without isolation of intermediate product. The reaction is carried out under an inert atmosphere of nitrogen and employing a slight molar excess (1-2%) of lithium salt than required by stoichiometry. The reaction is expected to be carried out in a 3-neck round bottom flask equipped with magnetic or mechanical stirring and effective heating/cooling system to control the rate of reaction. The reagents are added in continuous and dropwise manner, and are allowed to mix slowly to control the exothermicity of the reaction. The reaction mass is generally maintained below 60-80° C. After completing the addition, the reaction mixture is stirred for 1 hour at room temperature. The reaction mass is then heated to obtain a gentle reflux to ensure complete reaction. The crude product is expected to separate from the reaction mass upon cooling, and is then to be purified by using standard distillation and/or recrystallization techniques. The target product trimethylsilylmethyl-bis(isopropylphosphoamidinato)lanthanum is expected to be obtained in high yield and is expected to be substantially free of organic solvents (<0.5 ppm) as determined by FT-NMR and also substantially free of metallic impurities (<10 ppb) as determined by ICP-MS/ ICP-OES.

EXAMPLE 14

Organometallic compounds of the formula $(R^1YCR^2PR^3)_n M^{+m}L^1_{(m-n)}L^2_p$ listed in the following table are prepared according to the procedures provided in examples 1 through 14.

| Sample | M | $R^1$ | $R^2$ | $R^3$ | Y | $L^1$ | $L^2$ |
|---|---|---|---|---|---|---|---|
| A | Mg | i-Pr | Me | i-Pr | N | Cp | |
| B | Ga | Et | Me | Et | N | H | |
| C | Si | i-Pr | n-Bu | i-Pr | P | | |
| D | Te | i-Pr | Et | i-Pr | N | Me | |
| E | Cu | i-Pr | Me | i-Pr | P | | VTMS |
| F | Sc | Me | n-Bu | Et | P | TMG | |
| G | La | i-Pr | Me | i-Pr | N | TMPG | |
| H | Zr | i-Pr | t-Bu | i-Pr | P | Cp, Me | |
| I | Hf | i-Pr | Me | i-Pr | P | allyl, Me | isoprene |
| J | Nb | i-Pr | Et | i-Pr | N | Cp, Me | |
| K | Ta | i-Pr | t-Bu | i-Pr | P | Cp, Me | |
| L | W | i-Pr | Me | i-Pr | P | Cp, Me | |
| M | Ni | i-Pr | Me | i-Pr | N | | Bz, CO |
| N | Ru | c-Hx | t-Bu | c-Hx | P | $NO_3$ | p-cymene, COD |
| O | Pt | i-Pr | Me | i-Pr | N | $NO_3$ | |

In the above table, ligands separated by a comma denote that each ligand is present in that compound and TMG=tetramethylguanidinate and TMPG=tetramethylphosphoguanidinate.

EXAMPLE 15

Compositions suitable for use in ALD or direct liquid injection processes are prepared by combining certain of the compounds of Example 14 with certain organic solvents. The particular compositions are shown in the following table. The organometallic compounds are typically present in a concentration of 0.1 M for direct liquid injection.

| Composition Sample | Organometallic Compound Sample | Solvent |
|---|---|---|
| 1 | D | THF |
| 2 | D | 1,4-Dioxane |
| 3 | D | n-Butyl acetate |
| 4 | E | Octane |
| 5 | E | Diglyme |
| 6 | E | VTMS |
| 7 | F | THF |
| 8 | F | Octane |
| 9 | G | Diglyme |
| 10 | G | 2-Methoxyethoxy acetate |
| 11 | H | n-Butyl acetate |
| 12 | H | 2-Methoxyethoxy acetate |
| 13 | J | THF |
| 14 | K | Octane |
| 15 | K | Diglyme |
| 16 | M | n-Butyl acetate |
| 17 | M | 2-Methoxyethoxy acetate |
| 18 | O | Octane |
| 19 | O | THF |

What is claimed is:
1. A method of depositing a film comprising the steps of: providing a substrate in a vapor deposition reactor; conveying as a precursor an organometallic compound of the formula $(R^1YCR^2PR^3)_n M^{+m}L^1_{(m-n)}L^2_p$, wherein $R^1$, $R^2$ and $R^3$ are independently chosen from H, $(C_1-C_6)$ alkyl, $(C_2-C_6)$alkenyl, $(C_2-C_6)$alkynyl and aryl; Y=N or P; M=a metal; $L^1$=an anionic ligand; $L^2$=a neutral ligand; m=the valence of M; n=1-6; p=0-3; and wherein m>n in a gaseous form to the reactor; and depositing a film comprising the metal on the substrate.

2. The method of claim 1 wherein $L^1$ is chosen from hydride, halide, azide, alkyls, alkenyl, alkynyl, carbonyl, amido, alkylamido, dialkylamido, dialkylamidoalkyl, imido, hydrazido, phosphido, nitrosyl, nitryl, nitrate, nitrile, alkoxy, dialkylaminoalkoxy, alkoxyalkyldialkylamino, siloxy, diketonates, ketoiminates, cyclopentadienyls, silyls, pyrazolates, and amidinates.

3. The method of claim 1 wherein $L^2$ is chosen from CO, NO, alkenes, dienes, trienes, alkynes, and aromatic compounds.

4. The method of claim 1 wherein M is chosen from a Group 2 to Group 16 metal.

5. The method of claim 1 wherein the organometallic compound is in a composition further comprising an organic solvent; and wherein the method further comprises the step of conveying the composition into the reactor using direct liquid injection.

6. A method of depositing a film comprising the steps of: providing a substrate in a vapor deposition reactor; conveying as a first precursor an organometallic compound of the formula $(R^1YCR^2PR^3)_n M^{+m}L^1_{(m-n)}L^2_p$, wherein $R^1$, $R^2$ and $R^3$ are independently chosen from H, ($C_1$-$C_6$)alkyl, ($C_2$-$C_6$)alkenyl, ($C_2$-$C_6$)alkynyl and aryl; Y=N or P; M=a metal; $L^1$=an anionic ligand; $L^2$=a neutral ligand; m=the valence of M; n=1-6; p=0-3; and wherein m>n in a gaseous form to the reactor; chemisorbing the first precursor compound on the surface of the substrate; removing any non-chemisorbed first precursor compound from the reactor; conveying a second precursor in a gaseous form to the reactor; reacting the first and second precursors to form a film on the substrate; and removing any unreacted second precursor.

7. The method of claim 6 wherein the second precursor is selected from oxygen, ozone, water, peroxide, alcohols, nitrous oxide and ammonia.

8. The method of claim 6 wherein $L^1$ is chosen from hydride, halide, azide, alkyls, alkenyl, alkynyl, carbonyl, amido, alkylamido, dialkylamido, dialkylamidoalkyl, imido, hydrazido, phosphido, nitrosyl, nitryl, nitrate, nitrile, alkoxy, dialkylaminoalkoxy, alkoxyalkyldialkylamino, siloxy, diketonates, ketoiminates, cyclopentadienyls, silyls, pyrazolates, and amidinates.

9. The method of claim 6 wherein $L^2$ is chosen from CO, NO, alkenes, dienes, trienes, alkynes, and aromatic compounds.

10. The method of claim 6 wherein M is chosen from a Group 2 to Group 16 metal.

11. A method for preparing phosphoamidine compounds comprising reacting a nitrile compound with a primary phosphine in the presence of a metal trifluoromethanesulfonate catalyst.

12. The method of claim 11 further comprising reacting a primary amine with the nitrile compound and the primary phosphine.

* * * * *